(12) United States Patent
Urabe et al.

(10) Patent No.: US 10,813,625 B2
(45) Date of Patent: Oct. 27, 2020

(54) ULTRASOUND IMAGE DIAGNOSTIC APPARATUS

(71) Applicant: KONICA MINOLTA, INC., Chiyoda-ku (JP)

(72) Inventors: Makiko Urabe, Yokohama (JP); Kazushi Ota, Hino (JP); Manami Okada, Machida (JP)

(73) Assignee: Konica Minolta, Inc., Tokyo (JP)

( * ) Notice: Subject to any disclaimer, the term of this patent is extended or adjusted under 35 U.S.C. 154(b) by 464 days.

(21) Appl. No.: 15/283,790

(22) Filed: Oct. 3, 2016

(65) Prior Publication Data

US 2017/0100098 A1   Apr. 13, 2017

(30) Foreign Application Priority Data

Oct. 9, 2015   (JP) ................................ 2015-200682

(51) Int. Cl.
*A61B 8/00* (2006.01)
*A61B 8/08* (2006.01)

(52) U.S. Cl.
CPC .............. *A61B 8/468* (2013.01); *A61B 8/085* (2013.01); *A61B 8/0825* (2013.01); *A61B 8/469* (2013.01);
(Continued)

(58) Field of Classification Search
CPC ..... A61B 8/468; A61B 8/5223; A61B 8/0825; A61B 8/14; A61B 8/085; A61B 8/469;
(Continued)

(56) References Cited

U.S. PATENT DOCUMENTS

2005/0154305 A1\* 7/2005 Kamiyama ......... G01S 7/52071
600/443
2009/0076385 A1\* 3/2009 Jackson ............... A61B 8/0825
600/437
(Continued)

FOREIGN PATENT DOCUMENTS

JP   2001-120549   5/2001
JP   2002-095640   4/2002
(Continued)

OTHER PUBLICATIONS

Office Action dated May 28, 2019 issue in Japanese Patent Application No. 2015-200682.

*Primary Examiner* — Patricia J Park
*Assistant Examiner* — Victoria Fang
(74) *Attorney, Agent, or Firm* — Cozen O'Connor (57) ABSTRACT

An ultrasound image diagnostic apparatus includes the following. An ultrasound probe outputs transmission ultrasound into a subject in response to reception of a pulsed signal and outputs a reception signal in response to reception of ultrasound reflected from the subject. A transmitter generates the pulsed signal and outputs the generated pulsed signal to the ultrasound probe. A receiver receives the reception signal from the ultrasound probe and generates sound-ray data. An image generator generates ultrasound image data from the sound-ray data. An input receiver receives target position information on a target position. A highlighted-area determiner determines a first highlighted area among multiple areas in a body mark based on the target position information. A display combiner combines the body mark including the first highlighted area with the generated ultrasound image data and displays the resulting image on a display unit.

7 Claims, 9 Drawing Sheets

(52) U.S. Cl.
CPC ............ *A61B 8/5223* (2013.01); *A61B 8/463* (2013.01); *A61B 8/54* (2013.01)

(58) Field of Classification Search
CPC ......... A61B 8/54; A61B 8/463; A61B 5/0091; A61B 5/4312; A61B 6/502; A61B 10/0041; A61B 5/748; A61B 5/7485; G06T 2207/30068; Y10S 128/915
USPC .......................................................... 600/440
See application file for complete search history.

(56) References Cited

U.S. PATENT DOCUMENTS

| | | | |
|---|---|---|---|
| 2012/0262460 A1* | 10/2012 | Endo ...................... | A61B 5/055 345/441 |
| 2013/0237827 A1* | 9/2013 | Yamamori ........... | A61B 8/5207 600/450 |
| 2014/0088427 A1* | 3/2014 | Tashiro .................... | A61B 8/08 600/443 |
| 2014/0221835 A1* | 8/2014 | Ota ........................ | A61B 8/463 600/443 |
| 2015/0150531 A1* | 6/2015 | Futamura ............. | A61B 8/5261 378/37 |
| 2016/0110875 A1* | 4/2016 | Sugiyama ............ | A61B 8/0825 382/131 |

FOREIGN PATENT DOCUMENTS

| | | |
|---|---|---|
| JP | 2008-086742 | 4/2008 |
| JP | 2012-100815 | 5/2012 |
| JP | 2012-245205 | 12/2012 |
| JP | 2013-048762 | 3/2013 |
| JP | 2014-64637 | 4/2014 |
| JP | 2015-112123 | 6/2015 |

* cited by examiner

FIG.12

ULTRASOUND IMAGE DIAGNOSTIC APPARATUS

BACKGROUND OF THE INVENTION

Field of the Invention

The present invention relates to an ultrasound image diagnostic apparatus.

Description of Related Art

Ultrasound diagnosis, which is achieved by a simple operation with an ultrasound probe that is placed on the surface of the subject to acquire ultrasound images representing heart beat or movement of a fetus with high safety, can be repeated on the same subject. Ultrasound image diagnostic apparatuses which are used for such ultrasound diagnosis and which display ultrasound images are known.

An ultrasound diagnosis with a known ultrasound image diagnostic apparatus requires the examiner (examination technician or doctor) to conduct sequential scanning for generating ultrasound images of multiple sites of the subject in order and examinations of the ultrasound images. In the sequential examination procedures, an unskilled examiner may scan the body sites in a wrong order. To address the problem, the ultrasound image diagnostic apparatus used for the sequential examination procedures simultaneously displays scanned images of the body sites in chronological order in a single display area while highlighting the image corresponding to the site in a current examination procedure among the images of the body sites (refer to Japanese Patent Application Laid-Open No. 2014-64637).

The examination procedures for ultrasound diagnosis, for example, on the breast region, also may involve examinations in view of X-ray images and other diagnostic information acquired through other modalities or repeated examinations on the same patient every 6 or 12 months.

Unfortunately, the traditional ultrasound image diagnostic apparatus, which simply highlights the body site in chronological order, does not indicate target areas (sites) based on diagnostic results of other modalities and past ultrasound diagnosis. Thus, the ultrasound image diagnostic apparatus cannot inform the examiner of such target areas. Moreover, the ultrasound image diagnostic apparatus cannot preserve the records of the target areas (sites) that are closely observed during the diagnosis, for future reference.

BRIEF SUMMARY OF THE INVENTION

An object of the present invention is to indicate a target area (site) so that an examiner can readily perceive the position of the target area.

According to an aspect of the present invention, there is provided an ultrasound image diagnostic apparatus including: an ultrasound probe that outputs transmission ultrasound into a subject in response to reception of a pulsed signal and outputs a reception signal in response to reception of ultrasound reflected from the subject; a transmitter that generates the pulsed signal and outputs the generated pulsed signal to the ultrasound probe; a receiver that receives the reception signal from the ultrasound probe and generates sound-ray data; an image generator that generates ultrasound image data from the sound-ray data; an input receiver that receives target position information on a target position; a highlighted-area determiner that determines a first highlighted area among multiple areas in a body mark based on the target position information; and a display combiner that combines the body mark including the first highlighted area with the generated ultrasound image data and displays the resulting image on a display unit.

Preferably, in the ultrasound image diagnostic apparatus, the target position information indicates an area including a prior occurrence of a lesion or a lesion in the subject, among the multiple areas in the body mark.

Preferably, the ultrasound image diagnostic apparatus, further includes: an input unit that receives operation information; and a body-mark divider that segments the body mark into multiple areas in accordance with the operation information, wherein the highlighted-area determiner determines the first highlighted area among the multiple areas in the segmented body mark.

Preferably, in the ultrasound image diagnostic apparatus, the input receiver receives the target position information from another diagnostic apparatus, and the highlighted-area determiner determines the first highlighted area among the multiple areas in the body mark based on the received target position information.

Preferably, in the ultrasound image diagnostic apparatus, the input receiver reads the target position information from a first storage unit which stores the target position information on the subject, and the highlighted-area determiner determines the first highlighted area among the multiple areas in the body mark based on the read target position information.

Preferably, the ultrasound image diagnostic apparatus further includes: a controller that connects ultrasound image data to the multiple areas in the body mark and stores the resulting data in a second storage unit, the ultrasound image data being generated by examinations of sequential scanning of multiple target areas in the body mark.

Preferably, in the ultrasound image diagnostic apparatus, the highlighted-area determiner determines an area in a current examination procedure to be a second highlighted area, in the examinations performing the sequential scanning of the multiple target areas in the body mark for generation of ultrasound image data to be displayed, and the display combiner combines the body mark including the second highlighted area with the generated ultrasound image data and displays the resulting image on the display unit.

Preferably, the ultrasound image diagnostic apparatus further includes: an input unit that receives a predetermined input from an operator; and an output controller, wherein, the highlighted-area determiner determines a third highlighted area including a position corresponding to a lesion or a suspected lesion based on the input by the operator, and the output controller outputs the first highlighted area and the third highlighted area for simultaneous visual observation.

Preferably, the ultrasound image diagnostic apparatus further includes: a timing controller that counts the examination time of each of the areas; and an output controller, wherein, the highlighted-area determiner determines the area corresponding to the longest examination time counted by the timing controller to be a third highlighted area including a position corresponding to a lesion or a suspected lesion, and the output controller outputs the first highlighted area and the third highlighted area for simultaneous visual observation.

Preferably, in the ultrasound image diagnostic apparatus, the output controller combines the body mark including the third highlighted area with ultrasound image data generated corresponding to the third highlighted area and displays the resulting image on the display unit.

BRIEF DESCRIPTION OF THE DRAWINGS

The present invention will become more fully understood from the detailed description given hereinbelow and the appended drawings, and thus are not intended to define the limits of the present invention, and wherein.

DETAILED DESCRIPTION OF PREFERRED EMBODIMENTS

Embodiments of the present invention will now be described with reference to the accompanying drawings. The drawings should not be construed to limit the present invention.

Figure 1:
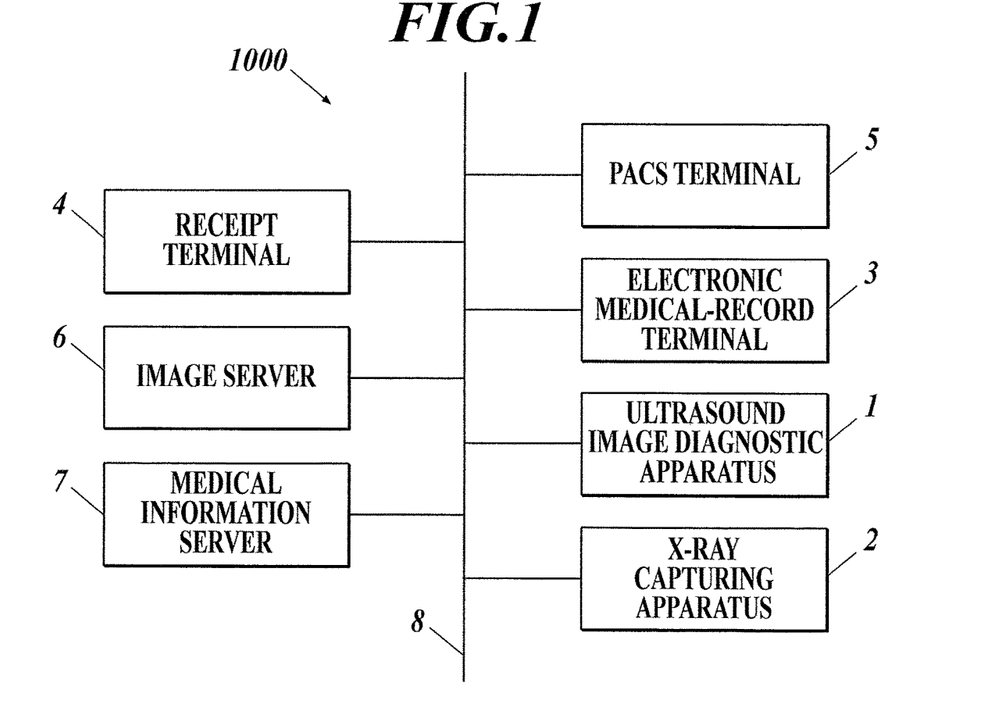
FIG. 1 is a block diagram illustrating a medical image management system according to an embodiment of the present invention.

A medical image management system 1000 to be installed in a medical facility, such as a hospital, will now be described with reference to FIG. 1. FIG. 1 is a block diagram illustrating the medical image management system 1000 according to this embodiment.

With reference to FIG. 1, the medical image management system 1000 includes an ultrasound image diagnostic apparatus 1, an X-ray capturing apparatus 2, an electronic medical-record terminal 3, a receipt terminal 4, a picture archiving and communication system (PACS) terminal 5, an image server 6, and a medical information server 7. The components of the medical image management system 1000 are connected via a local area network (LAN) 8, for example.

A typical communication scheme used in a hospital is a digital imaging and communication in medicine (DICOM). The communication between the components connected via LAN is established by DICOM modality worklist management (DICOM MWM) or DICOM modality performed procedure step (DICOM MPPS). Any other communication scheme may be used for this embodiment.

The receipt terminal 4 is installed on a reception desk of a medical facility. The electronic medical-record terminal 3 and the PACS terminal 5 are installed on the desk in an examination room in the medical facility. The image server 6, the medical information server 7, and the ultrasound image diagnostic apparatus 1 are installed at predetermined positions in the examination room. The X-ray capturing apparatus 2 is installed in an X-ray capturing room in the medical facility.

The receipt terminal 4 is used for calculation of insurance points and medical fees. The receptionist refers to a medical card of a patient, for example, and inputs the corresponding reception number, the name of the patient, and the patient ID to the receipt terminal 4. The receipt terminal 4 requests the medical information server 7 to transmit an electronic medical record or medical record data containing detailed information of the patient corresponding to the input name and the patient ID.

The medical information server 7 manages medical information. After the receipt terminal 4 receives the electronic medical record from the medical information server 7, the receptionist confirms the content of the electronic medical record on the display of the receipt terminal 4 and instructs the transmission of the electronic medical record from the receipt terminal 4 to the electronic medical-record terminal 3.

The electronic medical-record terminal 3 is installed on the examination desk in the examination room and is used by a doctor during diagnosis of a patient. The receipt terminal 4 transmits the electronic medical record of the patient to be examined to the electronic medical-record terminal 3. After the diagnosis of the patient, the receptionist inputs the information required for calculation of the medical fee and preparation of a receipt (calculation of medical points) to the receipt terminal 4 on the basis of the information in the electronic medical record. After inputting information required for the receipt, the receptionist confirms the medical bill appearing on the display of the receipt terminal 4, receives payment of the medical fee from the patient, and issues a medical receipt.

Upon updating of the medical record of the patient examined by the doctor, the electronic medical-record terminal 3 displays the content of the electronic medical record of the patient to be examined next in order of reception of electronic medical records from the receipt terminal 4. The doctor sees the patient and inputs the content of the diagnosis to the electronic medical-record terminal 3. The doctor radiographically examines the patient with the X-ray capturing apparatus 2, if necessary.

The X-ray capturing apparatus 2 captures an X-ray image of the patient (subject) in the X-ray capturing room and reads the captured image to generate X-ray image data. The X-ray capturing apparatus 2 is a mammographic apparatus or a computed radiographic (CR) apparatus, for example. The X-ray capturing apparatus 2 saves the X-ray image data acquired through the examination in the image server 6.

The image server 6 includes an image data base (DB) and stores image data, such as X-ray image data and ultrasound image data. The X-ray image data stored in the image server 6 is read by the PACS terminal 5. The PACS terminal 5 displays the corresponding X-ray image on the display. The doctor refers to the X-ray image displayed on the display of the PACS terminal 5 and inputs medical findings in the electronic medical-record terminal 3. After the diagnosis, the doctor inputs an instruction for the end of the diagnosis to the electronic medical-record terminal 3. In response, the electronic medical-record terminal 3 sends the electronic medical record to the receipt terminal 4.

During the diagnosis, the doctor carries out an ultrasound examination with the ultrasound image diagnostic apparatus 1, if necessary. The ultrasound image diagnostic apparatus 1 stores the ultrasound image data acquired through the examination in the image server 6. The ultrasound image data stored in the image server 6 is read by the PACS terminal 5. The PACS terminal 5 displays the corresponding ultrasound images on the display of the PACS terminal 5. The doctor refers to the ultrasound image displayed on the PACS terminal 5 and inputs medical findings in the electronic medical-record terminal 3.

In this embodiment, information instructing the doctor to conduct ultrasound examination on the patient is displayed on the ultrasound image diagnostic apparatus 1 in accordance with the examination information, such as the X-ray capturing data of the patient captured by the X-ray capturing apparatus 2 and the ultrasound image data acquired through scanning with the ultrasound image diagnostic apparatus 1. In some cases, examination history containing the results of examinations conducted in the past is recorded on physical paper. In such a case, the X-ray capturing apparatus 2, the electronic medical-record terminal 3, the receipt terminal 4, the PACS terminal 5, and the image server 6 may be removed from the medical image management system 1000.

Figure 2:
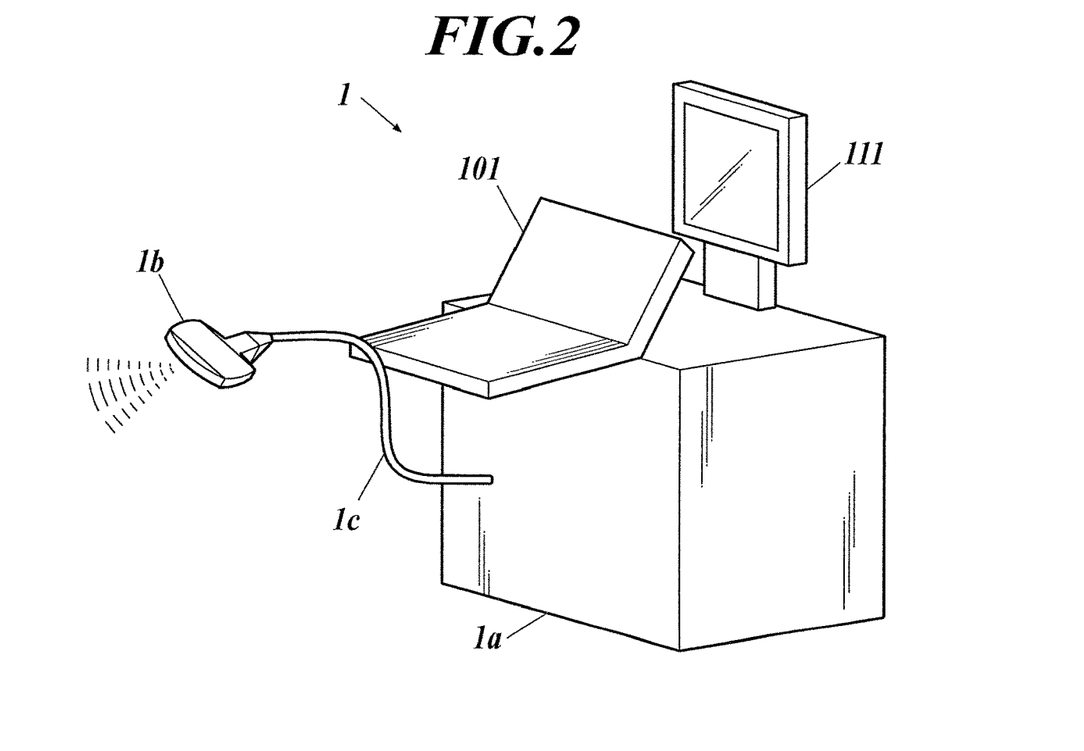
FIG. 2 is an external view of an ultrasound image diagnostic apparatus.
Figure 3:
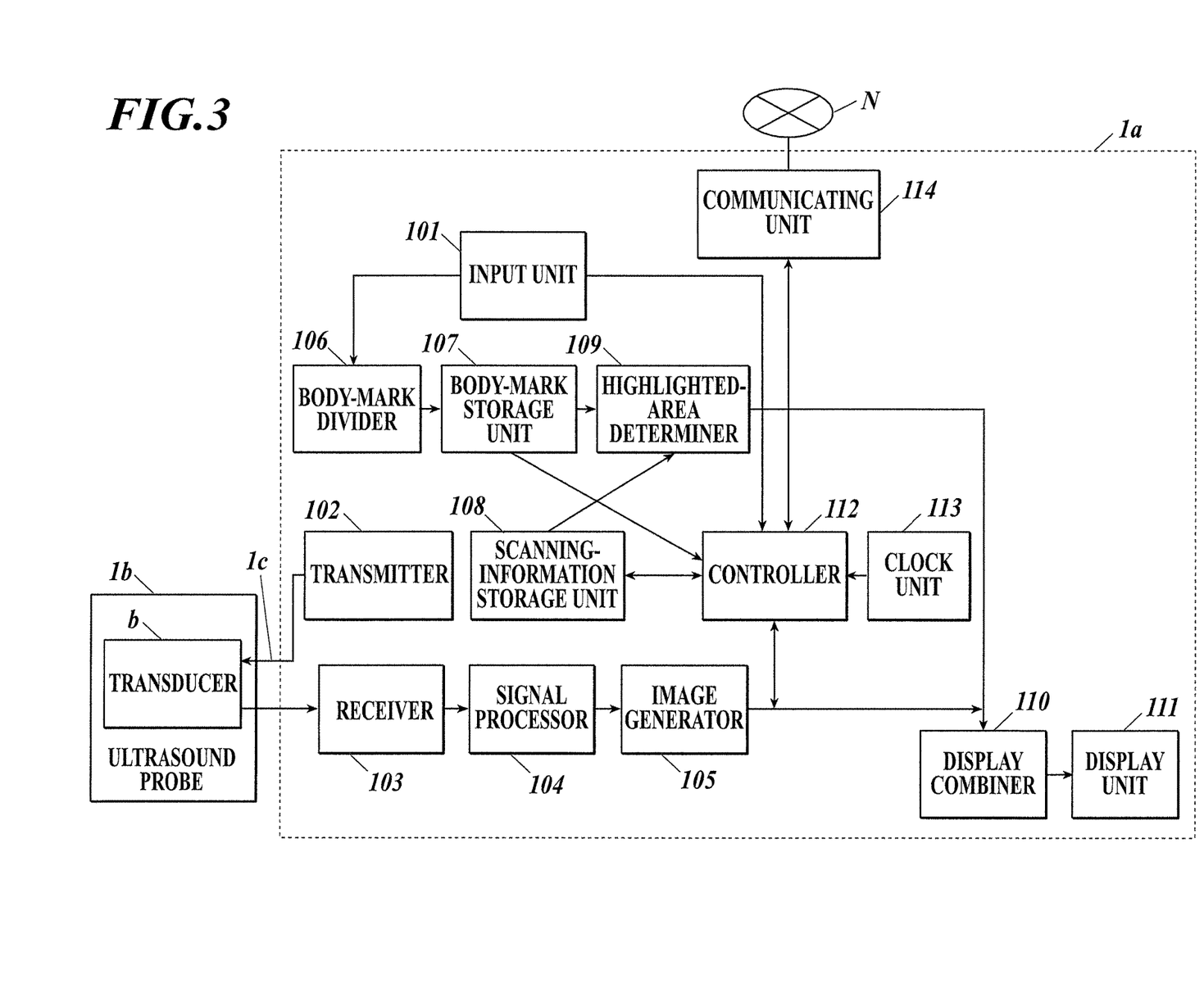
FIG. 3 is a block diagram illustrating the functional configuration of an ultrasound image diagnostic apparatus.

With reference to FIGS. 2 and 3, the ultrasound image diagnostic apparatus 1 will now be described in detail. FIG. 2 is an external view of the ultrasound image diagnostic apparatus 1. FIG. 3 is a block diagram illustrating the functional configuration of the ultrasound image diagnostic apparatus 1.

The ultrasound image diagnostic apparatus 1 outputs an ultrasound image representing the state of the internal anatomy of the living body of a patient (subject). That is, the ultrasound image diagnostic apparatus 1 transmits ultrasound (ultrasound waves) into the living body of the subject and receives ultrasound waves reflected from the subject (reflected ultrasound waves or echoes). The ultrasound image diagnostic apparatus 1 receives the reflected ultrasound waves, converts the received ultrasound waves to electrical signals, and generates ultrasound image data based on the electrical signals. The ultrasound image diagnostic apparatus 1 displays an ultrasound image representing the internal state of the subject on the basis of the generated ultrasound image data. The ultrasound image diagnostic apparatus 1 generates additional information associated with the generated ultrasound image data on the basis of information on the patient. The ultrasound image diagnostic apparatus 1 can add such information to the ultrasound image data to generate image files containing DICOM image data conforming to the DICOM specifications.

With reference to FIG. 3, the ultrasound image diagnostic apparatus 1 includes an ultrasound image diagnostic device 1*a* including an input unit 101 and a display unit 111, an ultrasound probe 1*b*, and a cable 1*c*. The ultrasound probe 1*b* transmits ultrasound waves into the subject and receives reflected ultrasound waves from the subject. The ultrasound image diagnostic device 1*a* is connected to the ultrasound probe 1*b* via the cable 1*c* and transmits an electrical driving signal to the ultrasound probe 1*b* to instruct the ultrasound probe 1*b* to transmit ultrasound waves into the subject. The ultrasound probe 1*b* generates electrical signals in response to the ultrasound waves reflected from the subject. The ultrasound image diagnostic device 1*a* receives the electrical signals (reception signal) from the ultrasound probe 1*b* and generates the ultrasound image data as described above.

The ultrasound probe 1*b* includes transducers b each composed of a piezoelectric device (see FIG. 3). The transducers b are disposed in a one-dimensional array along a direction (scanning direction), for example. In this embodiment, the ultrasound probe 1*b* includes 192 transducers b, for example. Alternatively, the transducers b may be disposed in a two-dimensional array. Any number of transducers b may be selected. In this embodiment, the ultrasound probe 1*b* is a linear electronic scanning probe that performs linear scanning of ultrasound. Alternatively, the ultrasound probe 1*b* may perform sector or convex scanning. The communication between the ultrasound image diagnostic device 1*a* and the ultrasound probe 1*b* may be established through wire communication with the cable 1*c*. Alternatively, the communication may be established through wireless communication, such as an ultra-wideband (UWB) scheme.

With reference to FIG. 3, the ultrasound image diagnostic device 1*a* includes an input unit 101, a transmitter 102, a receiver 103, a signal processor 104, an image generator 105, a body-mark divider 106, a body-mark storage unit 107, a scanning-information storage unit 108, a highlighted-area determiner 109, a display combiner 110, a display unit 111, a controller 112, a clock unit 113, and a communicating unit 114.

The input unit 101 includes various switches and buttons, a track ball, a mouse, and a keyboard for input of start commands for diagnosis and personal data of subjects, for example. The input unit 101 outputs operation signals to the controller 112.

The transmitter 102 is a circuit under the control of the controller 112 and supplies electrical driving signals to the ultrasound probe 1*b* via the cable 1*c* to cause the ultrasound probe 1*b* to generate ultrasound waves. The transmitter 102 includes a clock generating circuit, a delay circuit, and a pulse generating circuit, for example. The clock generating circuit generates clock signals for determining the transmission timing of driving signals and the frequency for transmission. The delay circuit determines delay times for the timings of transmitting driving signals through individual paths corresponding to the transducers and delays the transmission of the driving signals by the determined delay times, to converge a transmission beam consisting of ultrasound waves. The pulse generating circuit generates pulsed signals or driving signals in a predetermined cycle. The transmitter 102 having such a configuration drives some of the adjacent transducers b (for example, 64 of the 192 transducers) aligned in the ultrasound probe 1*b*, to generate ultrasound waves, for example. The transmitter 102 changes the transducers to be driven sequentially in the scanning direction every generation of ultrasound waves for scanning.

The receiver 103 is a circuit under the control of the controller 112 and receives the electrical signals from the ultrasound probe 1*b* via the cable 1*c*. The signal processor 104 is a circuit under the control of the controller 112 and processes the signals from the receiver 103 to generate sound-ray data. The signal processor 104 includes an amplifier, an A/D converter circuit, and a phased adder circuit, for example. The amplifier is a circuit that amplifies the signals received through the individual paths corresponding to the transducers by a predetermined amplification. The A/D converter circuit performs analog-to-digital conversion on the amplified signals. The phased adder circuit adds delay times to the A/D converted signals received through the individual paths corresponding to the transducers, to match the time phase, and adds (phased addition) the signals to generate sound-ray data.

Under the control of the controller 112, the image generator 105 converts the sound-ray data to brightness through envelope detection, logarithmic amplification, and adjustment of the dynamic range and gain on the sound-ray data from the signal processor 104, to generate B-mode ultrasound image data (B-mode image data). That is, the B-mode image data represents the intensity of the received signal in brightness. Alternatively, the image generator 105 may generate image data other than B-mode image data, such as A-mode image data, M-mode image data, or Doppler image data.

The body-mark divider 106 segments the body marks to be superposed on the ultrasound image on the basis of the information input via the input unit 101 or the communicating unit 114, under the control of the controller 112. The body-mark storage unit 107 is a semiconductor memory that stores the body marks segmented by the body-mark divider 106, under the control of the controller 112. The scanning-information storage unit 108 is a semiconductor memory that stores the ultrasound image data generated by the image generator 105 and the scanning information containing the examination time and operation of the ultrasound examination, under the control of the controller 112. The highlighted-area determiner 109 determines the area to be highlighted among the segmented areas of the body marks stored in the body-mark storage unit 107 and outputs the body marks containing the highlighted areas, under the control of the controller 112.

Under the control of the controller 112, the display combiner 110 establishes the display of the highlighted area of the body marks input by the highlighted-area determiner 109, combines the ultrasound image data generated by the image generator 105 and/or menu data generated by the controller 112 with the body marks, to generate combined image data, and outputs the combined image data to the display unit 111. The menu data generated by the controller 112 contains menu data other than ultrasound images, i.e., body marks 401 in a pre-examination menu 400 illustrated in FIG. 7, for example.

The display unit 111 may be a liquid crystal display (LCD), a cathode-ray tube (CRT) display, an organic electroluminescent (EL) display, an inorganic EL display, or a plasma display, for example. The display unit 111 displays images in the display area in accordance with image signals output from the display combiner 110.

The controller 112 includes a central processing unit (CPU), a read only memory (ROM), and a random access memory (RAM), for example. The controller 112 reads various processing programs, such as system programs stored in the ROM, loads these programs to the RAM, and comprehensively controls the operation of the components of the ultrasound image diagnostic apparatus 1 in accordance with the loaded programs. The ROM includes a non-volatile memory, such as a semiconductor, and stores system programs corresponding to the ultrasound image diagnostic apparatus 1, various sub-programs executable by the system programs, such as first and second pre-examination highlighting programs and a post-examination highlighting program, and various data items, such as gamma tables. These programs are stored in the form of program codes readable by a computer. The CPU operates in accordance with these program codes. The RAM provides a work area for temporarily storing the various programs to be executed by the CPU and data associated with these programs. For simplification of the drawing, the control lines from the controller 112 to the components are partially omitted in FIG. 3.

The clock unit 113 is a real-time clock that counts the current time and date and outputs information on the current time and date to the controller 112.

The communicating unit 114 includes a LAN adapter and communicates data among components via a network N, such as the LAN 8. The communicating unit 114 and the LAN 8 may support wire communication or wireless communication.

Some or all of the functional blocks of the transmitter 102, the receiver 103, the signal processor 104, the image generator 105, the body-mark divider 106, the highlighted-area determiner 109, the display combiner 110, the controller 112, the clock unit 113, and the communicating unit 114 of the ultrasound image diagnostic apparatus 1 can be provided as hardware circuits, such as integrated circuits. An example of an integrated circuit is a large scale integration (LSI) circuit. Depending on the degree of integration, the LSI circuit may be referred to as an IC, a system LSI circuit, a super LSI circuit, or an ultra LSI circuit. Any integration method other than LSI may be applied to the circuit. For example, a dedicated circuit or a general-purpose processor may be provided, or a reconfigurable processor that can reconfigure the connection and settings of a field programmable gate array (FPGA) and circuit cells in an LSI circuit may be used. Some or all of the functional blocks may be provided by software. In such a case, the software is stored in one or more storage media, such as a ROM, an optical disk, and a hard disk. The stored software is executed by a processor.

Figure 4:
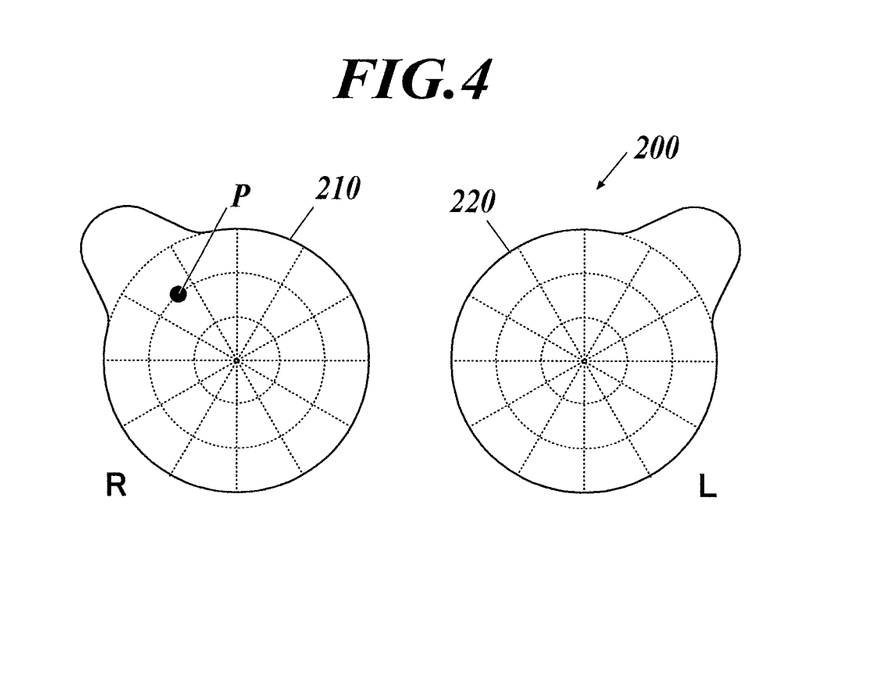
FIG. 4 illustrates body marks indicating breasts.
Figure 5:
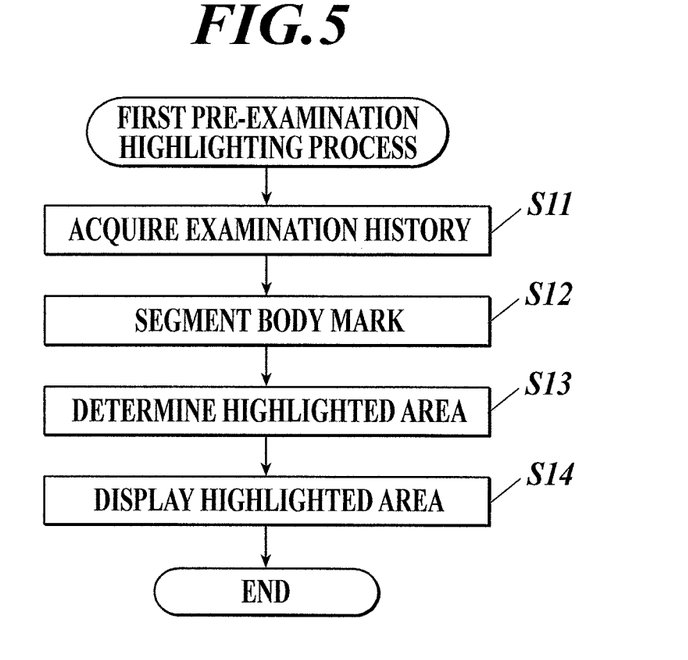
FIG. 5 is a flow chart illustrating a first pre-examination highlighting process.
Figure 6:
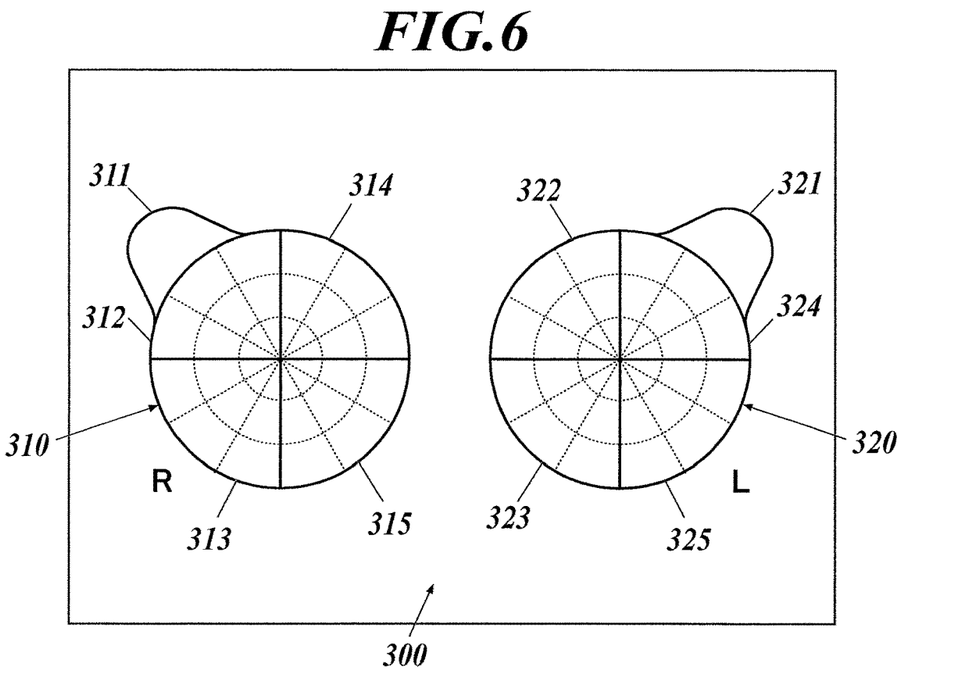
FIG. 6 illustrates body marks indicating breasts after segmentation.
Figure 7:
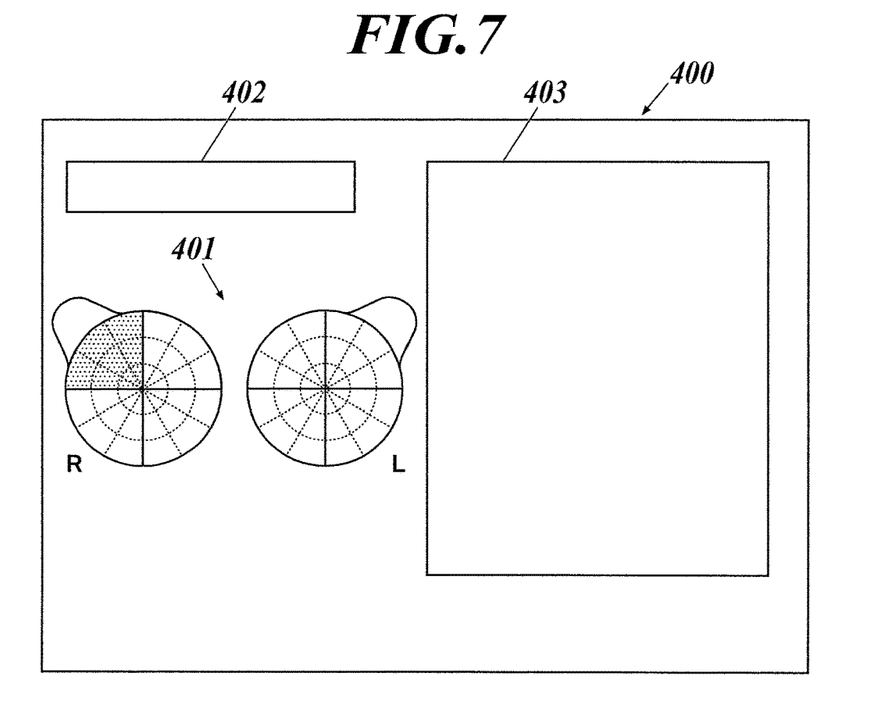
FIG. 7 illustrating a menu before start of examination procedures.

The operation of the medical image management system 1000 will now be described with reference to FIGS. 4 to 12. With reference to FIGS. 4 to 7, a first pre-examination highlighting process executed by the ultrasound image diagnostic apparatus 1 will now be described. FIG. 4 illustrates body marks 200 of breasts. FIG. 5 is a flow chart illustrating the first pre-examination highlighting process. FIG. 6 illustrates body marks 300 of breasts after segmentation. FIG. 7 illustrates a pre-examination menu 400.

In an examination process according to this embodiment, a patient requests an examination for breast cancer at a medical facility equipped with the medical image management system 1000; in the first examination on the patient, a doctor acquires X-ray image data of the breasts of the patient with the X-ray capturing apparatus 2; and in the second examination on the patient conducted at a later date, the doctor acquires ultrasound image data of the breasts of the patient with the ultrasound image diagnostic apparatus 1.

In the first examination, the X-ray image data on the breasts acquired with the X-ray capturing apparatus 2 is stored in the image server 6, and X-ray images based on the X-ray image data on the breasts appear on the PACS terminal 5. The doctor visually observes the X-ray images of the breasts on the PACS terminal 5 to determine a lesion and inputs lesion position information indicating the position of the lesion on the breasts as target position information to the electronic medical-record terminal 3. The electronic medical-record terminal 3 connects the information of the lesion position on the breast to the patient ID, the X-ray image data ID, and information on the date and time of capturing, and sends the information to the medical information server 7 to be stored.

During this operation, the X-ray image and the body marks 200 representing breasts, which are illustrated in FIG. 4, appear on the electronic medical-record terminal 3. The body marks 200 are a right body mark 210 of the right breast and a left body mark 220 of the left breast. The body marks 210 and 220 each include multiple unit areas, which are smallest segmentation units of the body marks.

For example, the doctor inputs a lesion position P on the right body mark 210 of the right breast. The lesion position information on the breast is stored in the medical information server 7 in the form of two-dimensional coordinates corresponding to the lesion position P on the body marks 200, for example.

The second examination is then conducted. In the second examination, different areas on the breasts are sequentially examined in the chronical order to acquire ultrasound image data of the areas.

In the second examination, the doctor and the patient are both in the same examination room, where the doctor uses the ultrasound image diagnostic apparatus 1 to examine the patient (subject). In such a case, an instruction for carrying out the first pre-examination highlighting process input by the user (doctor) via the input unit 101 triggers the controller 112 of the ultrasound image diagnostic apparatus 1 to carry out the first pre-examination highlighting process in accordance with the first pre-examination highlighting program stored in the ROM.

With reference to FIG. 5, the controller 112 receives the patient ID from the user via the input unit 101, requests the medical information server 7 to send examination history or lesion position information corresponding to the patient ID via the communicating unit 114, and receives the examination history from the medical information server 7 (Step S11). In this way, the communicating unit 114 may function as an input receiver that receives the target position information.

In response to the request for the examination history corresponding to the patient ID, the medical information server 7 reads the lesion position information corresponding to the patient ID in a storage unit (not shown) and sends this information to the ultrasound image diagnostic apparatus 1. Alternatively, in Step S11, the body-mark divider 106 may receive a manual input designating the examination history or lesion position information from the user via the input unit 101, request the medical information server 7 to send the lesion position information corresponding to the designation via the communicating unit 114, and receives the examination history. Alternatively, in Step S11, the body-mark divider 106 may receive the lesion position information directly input from the user via the input unit 101. For example, the user may refer to the electronic medical-record terminal 3 or a record on physical paper to input the lesion position information on the body marks displayed on the display unit 111 of the ultrasound image diagnostic apparatus 1. In this way, the input unit 101 may function as an input receiver that receives target position information on a target position.

The body-mark divider 106 displays body marks 300 representing breasts on the display unit 111, receives an instruction for segmentation of the body marks 300 into multiple areas from the user, segments the body marks 300 in accordance with the instruction, and stores the segmented body marks in the body-mark storage unit 107 (Step S12). With reference to FIG. 6, the body marks 300 are a right body mark 310 of the right breast and a left body mark 320 of the left breast. For example, in response to an instruction for designating at least one of the smallest segmentation units of the body marks 310 and 320, the body-mark divider 106 segments the right body mark 310 into areas 311, 312, 313, 314, and 315, and the left body mark 320 into areas 321, 322, 323, 324, and 325. Alternatively, in Step S12, the body-mark divider 106 may segment the body marks 300 on the basis of the input of the number of segments (for example, 10) in the body marks 300 or input of selection of a segmentation pattern among pre-set multiple patterns of the body marks 300 from the user via the input unit 101.

The highlighted-area determiner 109 reads the segmented body marks stored in the body-mark storage unit 107 and determines the area to be highlighted containing the lesion among the areas in the body marks segmented in Step S12 on the basis of the examination history or the lesion position information acquired in Step S11 (Step S13). In Step S13, the area to be highlighted is determined through alignment of the position of the lesion and the background of the body marks 300, where the reference point resides at the bottom left of the body marks 300, for example. For example, the area 312 of the body marks 300 illustrated in FIG. 6 is determined to be the highlighted area that corresponds to the position of the lesion position P illustrated in FIG. 4.

The display combiner 110 displays the body marks 300 including the highlighted area determined in Step S13 on the display unit 111 (Step S14) to terminate the first pre-examination highlighting process.

After the first pre-examination highlighting process, an examination involving capturing of ultrasound images starts. At this time, the body marks 300 including the highlighted area displayed in Step S14 continuously appear on the display unit 111. In the ultrasound image diagnostic apparatus 1, the transmitter 102, the receiver 103, the signal processor 104, the image generator 105, and the display combiner 110, display the real-time (live) ultrasound image data generated through the transmission and reception of ultrasound by the ultrasound probe 1b together with the body marks 300 including the area highlighted in Step S14 in an examination menu on the display unit 111, under the control of the controller 112.

In the examination procedures after the first pre-examination highlighting process, the pre-examination menu 400 appears on the display unit 111 as a register menu for patient information, as illustrated in FIG. 7, for example. The pre-examination menu 400 includes body marks 401 and information boxes 402 and 403. The body marks 401 correspond to the body marks 300 including the area 311 highlighted in Step S14. The information box 402 displays information such as the patient ID. The information box 403 displays information sent from the medical information server 7, such as a mammographic report (radiographic report of breast region) included in the medical findings of the patient to be examined, for example. The doctor conducts sequential examination procedures of the areas in the body marks 401 in order, while paying extra attention to the highlighted area 312 containing the lesion determined in the X-ray images.

The examination history referred to in the first pre-examination highlighting process may be a result of ultrasound examinations. In such a case, the first ultrasound examination is a usual ultrasound examination. The controller 112 receives the lesion position information diagnosed through the ultrasound examination from the user or doctor via the input unit 101, connects the position of the lesion to the patient ID of the patient to be examined, and stores the position in the scanning-information storage unit 108 or the medical information server 7. In the second ultrasound examination of the same patient conducted after 6 or 12 months, the first pre-examination highlighting process is carried out at the ultrasound image diagnostic apparatus 1. At this time, the controller 112 acquires the lesion position information corresponding to the patient ID of the patient who received the first ultrasound examination, as the examination history from the scanning-information storage unit 108 or the medical information server 7, in Step S11. In this way, the controller 112 functions as an input receiver, and the scanning-information storage unit 108 functions as a first storage unit that stores target position information.

The lesion position information as the target position information may be the position of something other than an actual lesion, such as a suspected lesion, a prior occurrence of a lesion, or a prior occurrence of a suspected lesion.

The highlighted-area determiner 109 may acquire the breast density of the patient and assign different colors to the highlighted areas corresponding to the target position information depending on the breast density. For example, high breast density may be displayed in a first color, whereas low breast density may be displayed in a second color. The highlighted-area determiner 109 may assign different colors to the highlighted areas depending on diagnostic information, such as category, based on a prior examination. For example, a lesion in the benign category may be a highlighted area in a third color and a lesion in the malignant category may be displayed in a fourth color. Besides the category, the diagnostic information may indicate shades of the suspected lesion or the size and shape of the lesion. The highlighted-area determiner 109 can receive the information on the patient or the diagnostic information from the input unit 101 or the medical information server 7 via the communicating unit 114. The highlighted-area determiner 109 can acquire the information on the patient or the diagnostic information through analysis of image data sent from the medical information server 7. For example, breast density can be estimated through analysis of the distribution of brightness in an image captured by the X-ray capturing apparatus 2 and/or an image captured by the ultrasound image diagnostic apparatus 1, and the characteristics of the lesion can be detected through machine learning techniques. For example, the scanning-information storage unit 108 stores a database connecting the breast density and the category with color, and the highlighted-area determiner 109 refers to the database to determine (change) the color of the highlighted area in accordance with the breast density or the category. Besides color, the highlighted-area determiner 109 may change the pattern (e.g., density of hatched lines, dots, or other patterns filling the area) of the highlighted area. In this way, the target position information can be visually observed with higher precision.

Figure 8A:
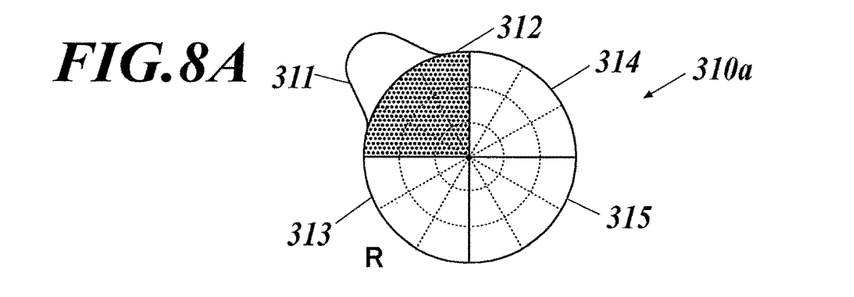
FIG. 8A is a first body mark indicating a right breast.
Figure 8B:
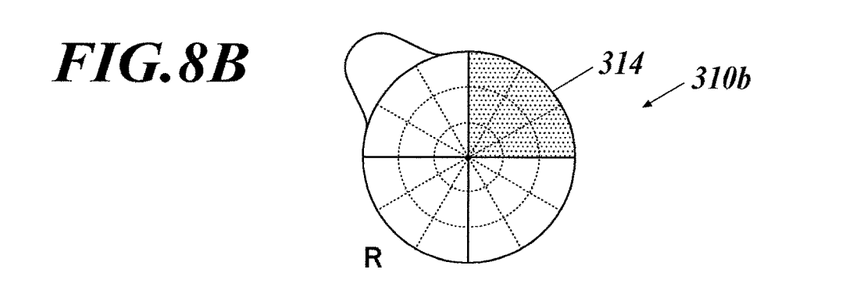
FIG. 8B is a second body mark indicating the right breast.
Figure 8C:
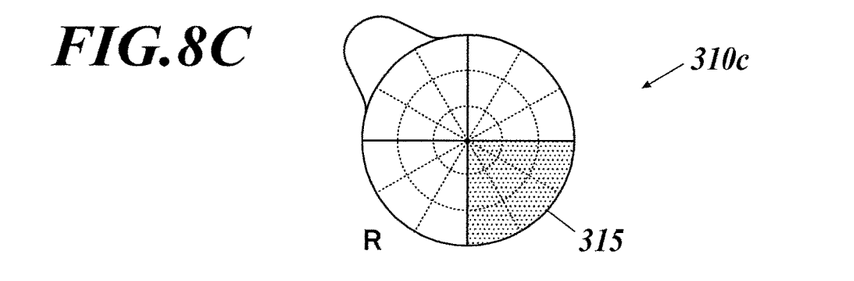
FIG. 8C is a third body mark indicating the right breast.
Figure 8D:
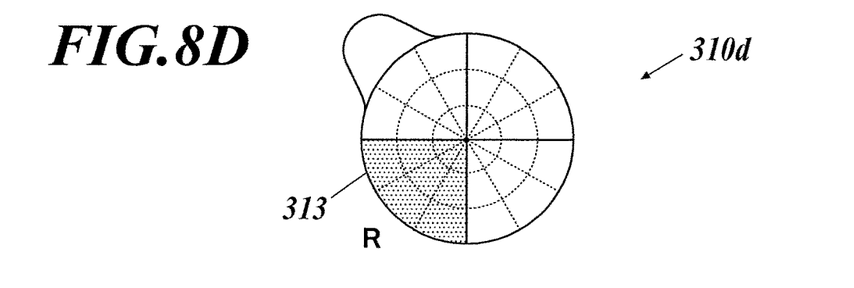
FIG. 8D is a fourth body mark indicating the right breast.
Figure 8E:
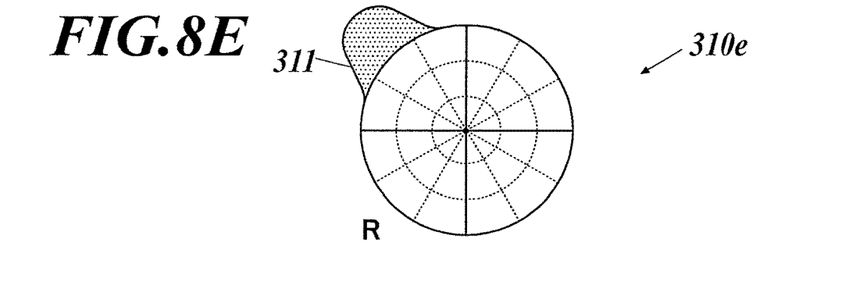
FIG. 8E is a fifth body mark indicating the right breast.
Figure 9:
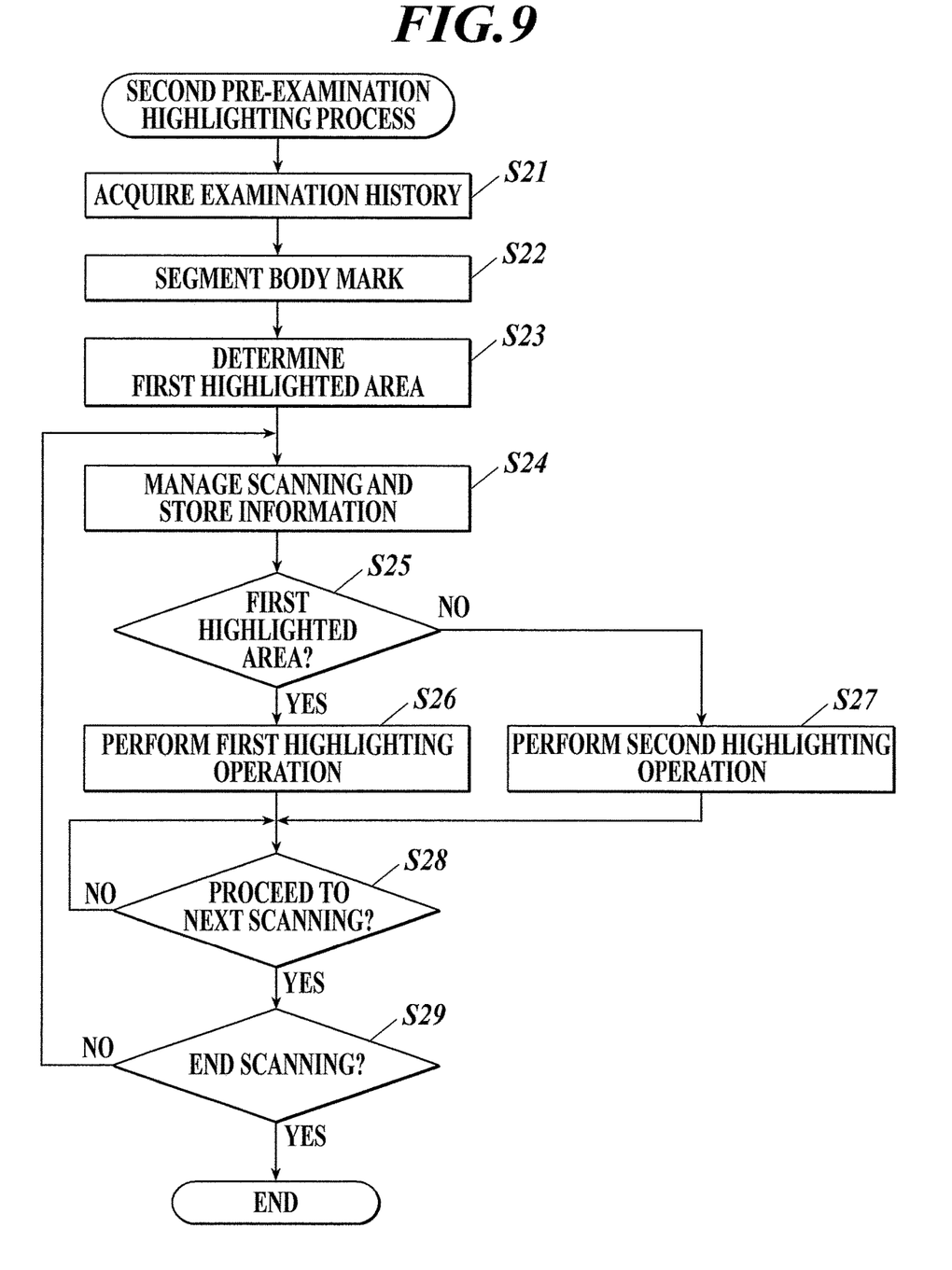
FIG. 9 is a flow chart illustrating a second pre-examination highlighting process.
Figure 10:
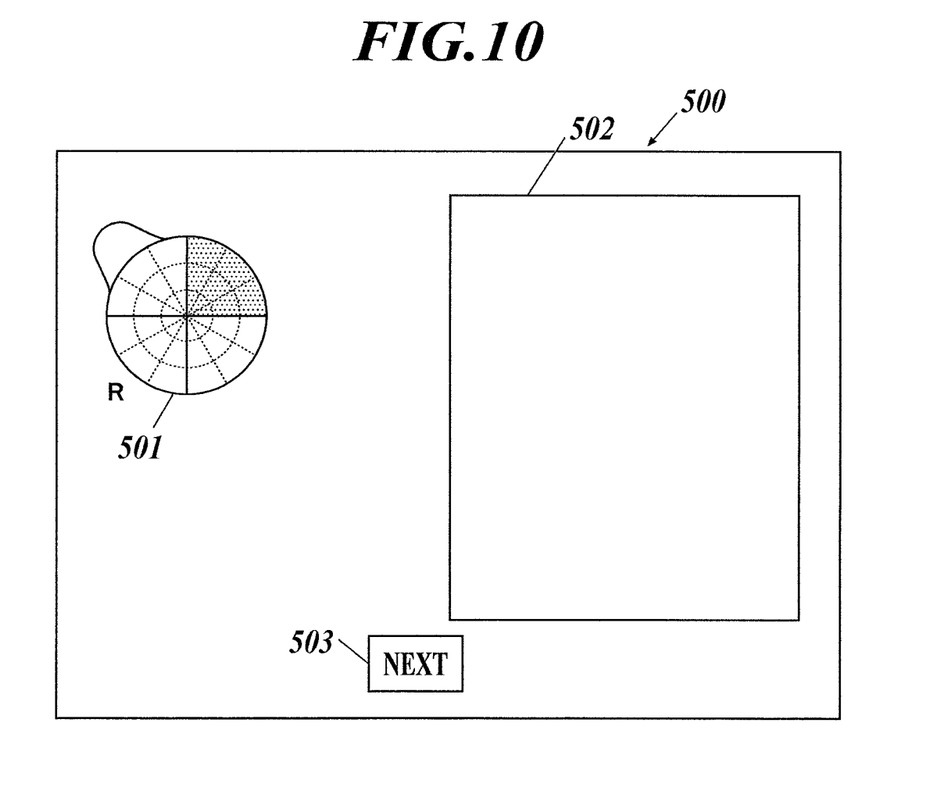
FIG. 10 illustrates a menu during examination.

With reference to FIGS. 8A to 10, a second pre-examination highlighting process to be carried out at the ultrasound image diagnostic apparatus 1 will now be described. FIG. 8A is a first right body mark 310a indicating the right breast. FIG. 8B is a second right body mark 310b indicating the right breast. FIG. 8C is a third right body mark 310c indicating the right breast. FIG. 8D is a fourth body mark 310d indicating the right breast. FIG. 8E is a fifth right body mark 310e indicating the right breast. FIG. 9 is a flow chart illustrating the second pre-examination highlighting process. FIG. 10 illustrates a progress management menu 500.

The second pre-examination highlighting process involves highlighting an area of the body marks on the basis of a past diagnostic result and managing the progress of the sequential examination procedures of the ultrasound images of the examined body sites. An example order of the sequential examination procedures of ultrasound images will now be described with reference to FIGS. 8A to 8E.

Ultrasound examinations on sites of the subject in the highlighted areas of the body marks are conducted in the sequential order of FIGS. 8A, 8B, 8C, 8D, and 8E. Each of the body marks 310a, 310b, 310c, 310d, and 310e in FIGS. 8A, 8B, 8C, 8D, and 8E, respectively, includes areas 311, 312, 313, 314, and 315. In this description, the areas in the body marks subjected to the sequential examination procedures are highlighted in two different ways. The area of the subject in a current examination procedure and including the position of a lesion diagnosed through a past examination is displayed with a first highlight. The area of the subject in the current examination procedure is displayed with a second highlight. The area with the first highlight (first highlighted area) and the area with the second highlight (second highlighted area) are presented in different colors and/or patterns.

The area 312 of the right body mark 310a is displayed with the first highlight. The areas 314, 315, 313, and 311 of the respective body marks 310b, 310c, 310d, and 310e are displayed with the second highlight. In these examples, five areas are defined in each breast for the sequential ultrasound examination procedures.

The first and second examinations are also conducted in the second pre-examination highlighting process. The first examination is the same as that in the first pre-examination highlighting process. In the second examination, the doctor and the patient are both in the same examination room, where the doctor uses the ultrasound image diagnostic apparatus 1 to examine the patient (subject). In such a case, an instruction for carrying out the second pre-examination highlighting process input by the user (doctor) via the input unit 101 triggers the controller 112 to carry out the second pre-examination highlighting process in accordance with the second pre-examination highlighting display program stored in the ROM.

Steps S21 and S22 in FIG. 9 are the same as Steps S11 and S12 in FIG. 5, respectively. The highlighted-area determiner 109 determines the area to be displayed with the first highlight among the areas in the body marks defined in Step S22, on the basis of the examination history or the lesion position information acquired in Step S21 (Step S23).

The controller 112 displays a progress management menu of a current ultrasound examination procedure (the order of the sequential ultrasound examination procedures) on the display unit 111, instructs the transmitter 102, the receiver 103, the signal processor 104, the image generator 105, and the display combiner 110 to display the body marks and real-time ultrasound image data generated through transmission and reception of ultrasound by the ultrasound probe 1b on the progress management menu, starts counting the duration of the current examination procedure with reference to the current time and date sent from the clock unit 113, receives an input operation from the user via the input unit 101, carries out processing corresponding to the input operation (for example, storing (saving) data on any ultrasound image frame in the real-time ultrasound image data in the scanning-information storage unit 108), and starts storing the information on the input operation or scanning information in the scanning-information storage unit 108 (Step S24). In Step S24 carried out immediately after Step S28 involving switching to the next examination, the controller 112 refers to the current time and date sent from the clock unit 113 to end the counting of duration of the previous examination and stores the time of the previous examination as scanning information in the scanning-information storage unit 108. The controller 112 connects the scanned ultrasound image data to the areas in the body marks and stores the resulting data in the scanning-information storage unit 108. For example, the scanning-information storage unit 108 stores a database containing the numbers of the areas in the body marks connected to the ultrasound image data. In this way, the scanning-information storage unit 108 also functions as a second storage unit that connects the ultrasound image data to the areas in the body marks and stores the ultrasound image data.

The first and second storage units may have the same configuration as the scanning-information storage unit 108 or any other configuration. The first storage unit may have a different configuration from the second storage unit.

The current progress management menu displayed in Step S24 is the progress management menu 500 illustrated in FIG. 10, for example. The progress management menu 500 includes a body mark 501, an ultrasound image 502, and a "next" button 503. The body mark 501 includes a second highlighted area to be currently examined. The body mark 501 is identical to the right body mark 310*b* in FIG. 8B in the second examination procedure, for example. The ultrasound image 502 is a real-time ultrasound image. The "next" button 503 is clicked to switch to the next area (to proceed to the next examination in order). Other than clicking the "next" button 503, a hard key of the input unit 101 may be operated to proceed to the next area.

The highlighted-area determiner 109 determines whether the current highlighted area in the body mark in the progress management menu displayed in Step S24 is the first highlighted area determined in Step S23, on the basis of the scanning information on the current examination stored in the scanning-information storage unit 108 (Step S25). If the current highlighted area is the first highlighted area (YES in Step S25), the display combiner 110 displays the current area with the first highlight in the body mark in the current progress management menu displayed in Step S24 (Step S26). If the current highlighted area is not the first highlighted area (NO in Step S25), the display combiner 110 displays the current area with the second highlight in the body mark in the current progress management menu displayed in Step S24 (Step S27). The highlighted-area determiner 109 determines whether to proceed to the next examination depending on the clicking of the "next" button 503 by the user via the input unit 101, on the basis of the scanning information on the current examination stored in the scanning-information storage unit 108 (Step S28). If the current area is not switched to the next area (NO in Step S28), the process repeats Step S28.

If the current area is switched to the next area (YES in Step S28), the highlighted-area determiner 109 determines whether to end the scanning in the sequential examination procedures on the basis of whether the current examination is the last examination (Step S29). If the scanning is not to end (NO in Step S29), the process goes to Step S24 and the current area is switched to the next area. If the scanning is to end (YES in Step S29), the second pre-examination highlighting process ends.

The examination history referred to in the second pre-examination highlighting process may be the information on the ultrasound examination acquired in Step S21, as in the first pre-examination highlighting process.

In response to an instruction for displaying ultrasound images input to the ultrasound image diagnostic apparatus 1 via the input unit 101 after the second pre-examination highlighting process, the highlighted-area determiner 109 reads the ultrasound image data acquired through scanning of the areas during the second pre-examination highlighting process and the scanning information in the scanning-information storage unit 108, and the display combiner 110 displays the ultrasound image data on the areas and the scanning information on the areas on the display unit 111.

Figure 11:
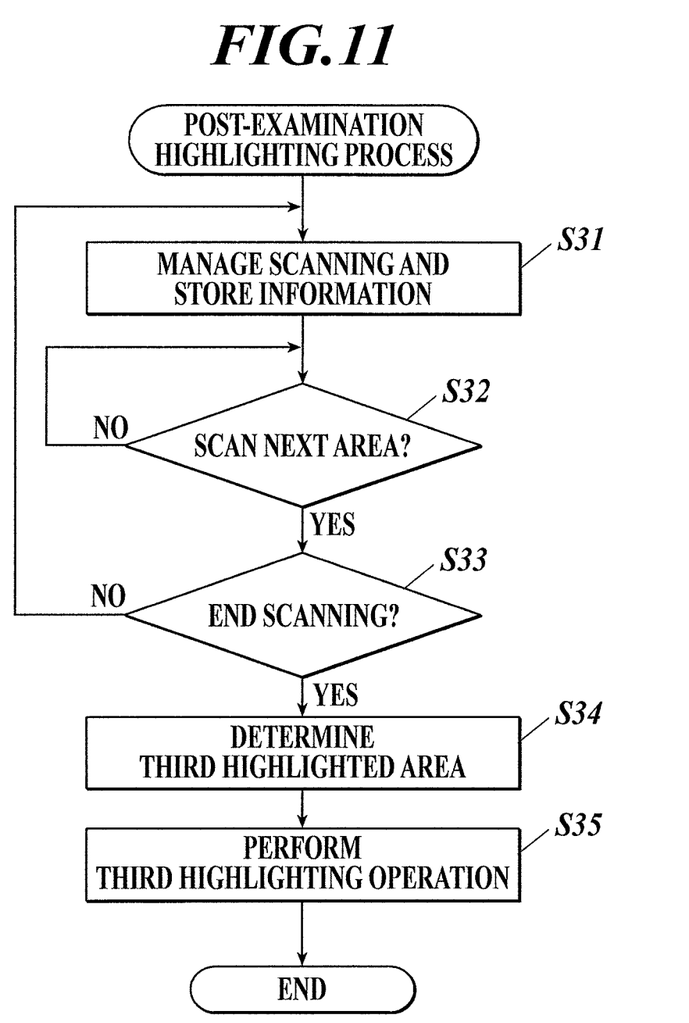
FIG. 11 is a flow chart illustrating a post-examination highlighting process.
Figure 12:
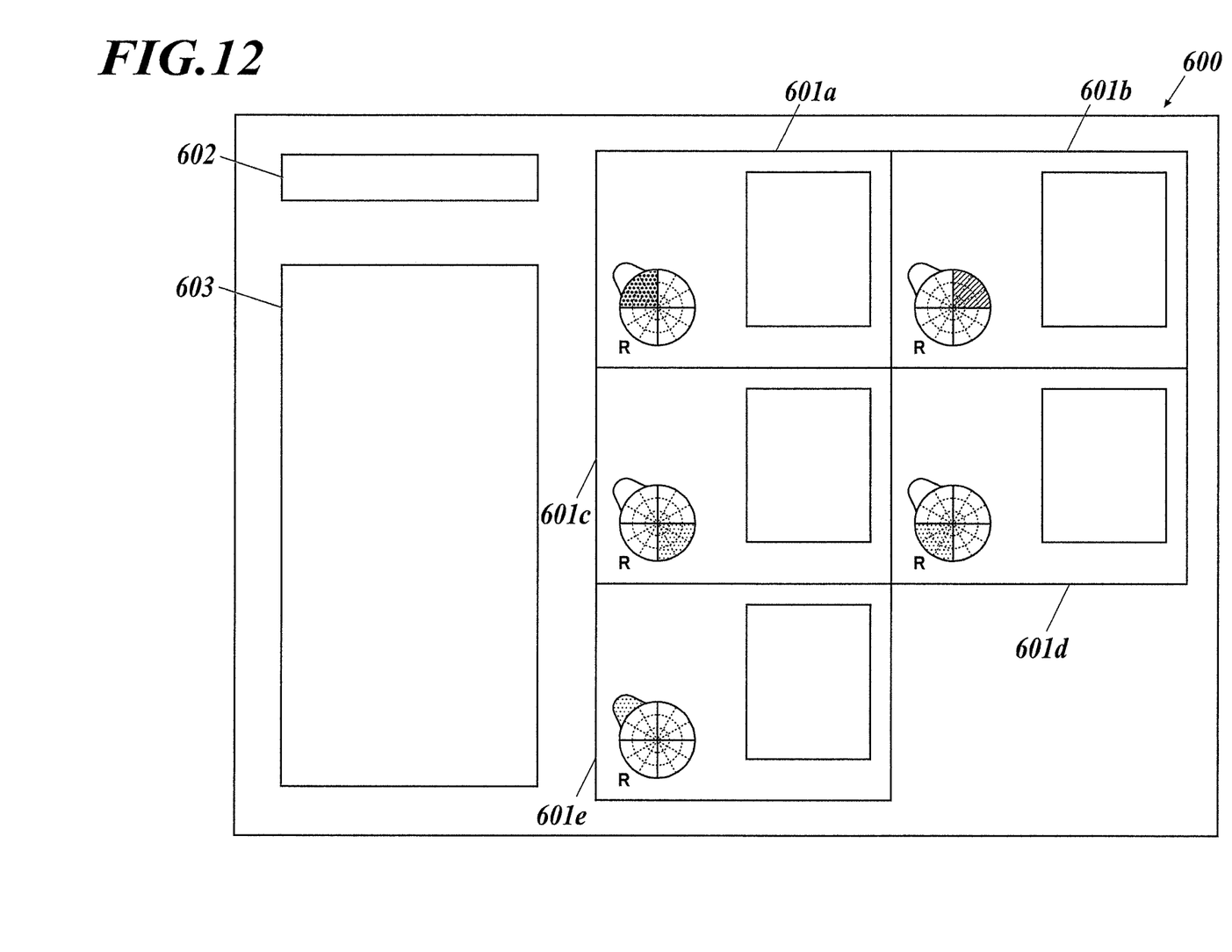
FIG. 12 illustrates examination results.

A post-examination highlighting process carried out in the ultrasound image diagnostic apparatus 1 will now be described with reference to FIGS. 11 and 12. FIG. 11 is a flow chart illustrating the post-examination highlighting process. FIG. 12 illustrates an examination result menu 600.

An object of the present invention (i.e., readily informing an examiner of the position of target area (site)) can be achieved even without the post-examination highlighting process described in the following. The post-examination highlighting process is preferred for ready confirmation of the position of a target area (site) by the examiner after the examination in addition to before the examination. The post-examination highlighting process can eliminate the first and second pre-examination highlighting processes described above. That is, an object of the present invention can be achieved through the post-examination highlighting process without the first and second pre-examination highlighting processes.

After the ultrasound examination, the post-examination highlighting process is carried out to display an ultrasound image data item satisfying predetermined conditions indicating that the data item is a target data item specified by the examiner, among the ultrasound image data items acquired through the sequential examination procedures, together with a body mark including a highlighted area corresponding to the site captured in the ultrasound image data. The predetermined conditions refer to a predetermined duration of the ultrasound examination of the ultrasound image data item or a predetermined operation, such as saving the ultrasound image data item, for example. For example, the first examination is the same as that in the first pre-examination highlighting process, but the lesion position information determined in the X-ray image capturing in the first examination should not be referred to in the post-examination highlighting process.

In the second examination, the doctor and the patient are both in the same examination room, where the doctor uses the ultrasound image diagnostic apparatus 1 to examine the patient (subject). In such a case, an instruction for carrying out the post-examination highlighting process input by the user (doctor) via the input unit 101 triggers the controller 112 to start the post-examination highlighting process.

Steps S31, S32, and S33 in FIG. 11 are the same as Steps S24, S28, and S29 in FIG. 9, respectively. If the sequential ultrasound examination procedures are finished (YES in Step S33), the highlighted-area determiner 109 reads the scanning information stored in the scanning-information storage unit 108 in Step S31. In accordance with the scanning information containing the duration and operation information of the examination procedures, the highlighted-area determiner 109 determines at least one third-highlighted area corresponding to the examination procedure having the longest duration and/or the examination procedure having a specific operation, such as saving the ultrasound image data (Step S34). The third highlighted area is presented in a color and/or pattern different from those of the first and second highlighted areas. The third highlighted area may be presented in a different color and/or pattern depending on the duration of the ultrasound examinations and the presence of a specific operation in the ultrasound examinations, or depending on the duration of the ultrasound examination or the type of operation conducted.

The highlighted-area determiner 109 reads the ultrasound image data acquired through the ultrasound scanning performed in Step S31 in the scanning-information storage unit 108, and the display combiner 110 generates to display an examination result menu on the display unit 111 (Step S35). The examination result menu shows the body marks of the ultrasound examinations in connection with the ultrasound image data of the ultrasound examinations. The body marks include the first highlighted area identical to that in the progress management menu in Step S31 and the third highlighted area determined in Step S34. The post-examination highlighting process then ends.

Similar to the first and second pre-examination highlighting processes, the first highlighted area may be displayed on the basis of the lesion position information as the target position information in the post-examination highlighting process. In such a case, the examination result menu displayed in Step S35 is the examination result menu 600 in FIG. 12, for example. The examination result menu 600 includes ultrasound image boxes 601a, 601b, 601c, 601d, and 601e and information boxes 602 and 603.

The ultrasound image boxes 601a, 601b, 601c, 601d, and 601e contain body marks corresponding to the sequential examination procedures and ultrasound images based on the ultrasound image data stored during the sequential examination procedures. The body marks in the ultrasound image boxes 601c, 601d, and 601e include second highlighted areas respectively corresponding to the areas 315, 313, and 311 in the body marks 300 in FIG. 6. The body mark in the ultrasound image box 601a includes a first highlighted area corresponding to the area 312 in the body marks 300 in FIG. 6. The body mark in the ultrasound image box 601b includes a third highlighted area corresponding to the area 314 in the body marks 300 in FIG. 6.

According to the embodiment described above, the ultrasound image diagnostic apparatus 1 includes an ultrasound probe 1b, a transmitter 102, a receiver 103, a signal processor 104, an image generator 105, an input receiver that receives target position information, a highlighted-area determiner 109 that determines a first highlighted area among multiple areas in a body mark on the basis of the target position information, and a display combiner 110 that combines the body mark including the first highlighted area with real-time ultrasound image data and displays the resulting image on a display unit 111. Such an ultrasound image diagnostic apparatus 1 facilitates the visual confirmation of the target area (site) with the first highlight by the examiner or doctor (user) before the ultrasound examination, and improves the precision and efficiency of the ultrasound examination of the first highlighted area.

The target position information indicates an area including a prior occurrence of a lesion or a prior occurrence of a suspected lesion in the subject, among the multiple areas in the body mark. By observing the first highlighted area before the ultrasound examination, the examiner or doctor can readily confirm the target area (site) based on the prior examinations, and the ultrasound examination can be conducted on the first highlighted area with high precision and high efficiency.

The ultrasound image diagnostic apparatus 1 includes a body-mark divider 106 that segments a body mark into multiple areas in accordance with the operation of the input unit 101. The highlighted-area determiner 109 determines the first highlighted area among multiple areas in the segmented body mark. The body mark can be segmented into any multiple areas that can be presented as first highlighted areas. Ultrasound examinations can be conducted on the first highlighted areas with high precision and high efficiency in accordance with the segmented areas.

In the ultrasound image diagnostic apparatus 1, the communicating unit 114 receives target position information in the subject from the medical information server 7, which is another diagnostic apparatus, and the highlighted-area determiner 109 determines the first highlighted area among multiple areas in the body mark on the basis of the received target position information. Such automatic determination of the first highlighted area can reduce the burden of the examiner, and achieve ultrasound examinations with high precision and high efficiency in view of diagnostic results of another diagnostic apparatus.

In the ultrasound image diagnostic apparatus 1, the controller 112 reads target position information from the scanning-information storage unit 108, which stores the target position information of the subject, and the highlighted-area determiner 109 determines the first highlighted area among the multiple areas in the body mark on the basis of the target position information. In this way, the ultrasound examinations can be conducted with high precision and high efficiency in view of the target position information.

Alternatively, the input unit 101 may receive an input of target position information from the examiner or doctor, and the highlighted-area determiner 109 may determine the first highlighted area among the multiple areas in the body mark on the basis of the target position information.

In the sequential examination procedures of scanning the target areas in the body mark for generation of ultrasound image data with the ultrasound image diagnostic apparatus 1, the controller 112 connects the ultrasound image data to the areas in the body mark and stores the ultrasound image data in the scanning-information storage unit 108. Since the ultrasound image data is stored in the scanning-information storage unit 108 in connection with the areas, the ultrasound image data connected to the area assigned by the operator can be retrieved from the scanning-information storage unit 108 and displayed on the display unit 111.

In the sequential examination procedures of scanning the target areas in the body mark for generation of ultrasound image data with the ultrasound image diagnostic apparatus 1, the highlighted-area determiner 109 determines the currently examined area to be the second highlighted area, and the display combiner 110 combines the body mark including the second highlighted area with the real-time ultrasound image data and displays the resulting image on the display unit 111. Thus, the examiner can visually observe the second highlighted area during the ultrasound examination and can readily confirm the current target area. Moreover, each ultrasound examination procedures of the target area can be conducted with high precision and high efficiency.

The ultrasound image diagnostic apparatus 1 includes an input unit 101 that receives a predetermined input from the operator, a highlighted-area determiner 109 that determines a third highlighted area including a position corresponding to a lesion or a suspected lesion on the basis of the input by the operator, and a display combiner 110 that outputs the first highlighted area and the third highlighted area to the display unit 111 for simultaneous display. Thus, the user can readily and simultaneously observe the first highlighted area and the third highlighted area based on the input by the operator.

The ultrasound image diagnostic apparatus 1 includes a controller 112 that counts the examination time for each area, a highlighted-area determiner 109 that determines the area that requires the longest examination time to be a third highlighted area including a position corresponding a lesion or a suspected lesion, and a display combiner 110 that outputs the first and third highlighted areas to the display unit 111 for simultaneous display. In this way, the display combiner 110 also functions as an output controller. Thus, the user can readily and simultaneously observe the first highlighted area and the third highlighted area, which requires the longest examination time.

The controller 112 may generate a report enabling simultaneous visual observation of the first and third highlighted areas and send the report to a printer (not shown) for print out. In such a case, the controller 112 functions as an output controller.

The display combiner 110 of the ultrasound image diagnostic apparatus 1 combines the body mark including the third highlighted area with the ultrasound image data generated during the examination on to the third highlighted area, and displays the resulting image on the display unit 111. Thus, the user can readily observe the third highlighted area having a long examination time or an input operation, after the sequential examination procedures, and can diagnose the ultrasound image of this area with high precision and high efficiency.

The ultrasound image diagnostic apparatus according to the embodiments described above should not be construed to limit the present invention.

For example, the body marks 310b to 310e respectively illustrated in FIGS. 8A to 8E each include only a second highlighted area. Alternatively, the body marks may include other highlighted areas. For example, the body marks 310b to 310e may include a first highlighted area (in the area 312) in addition to the second highlighted area.

The detailed configuration and detailed operation of the components constituting the medical image management system 1000 according to the embodiments described above may be modified in various ways without departing from the scope of the invention.

The present U.S. patent application claims priority under the Paris Convention of Japanese Patent Application No. 2015-200682 filed on Oct. 9, 2015 the entirety of which is incorporated herein by reference.

What is claimed is:

1. An ultrasound image diagnostic apparatus which outputs transmission ultrasound into a subject and which generates ultrasound image data based on ultrasound reflected from the subject, the apparatus comprising:
  an input receiver configured to receive target position information on a target position regarding the subject;
  a highlighted-area determiner configured to: (i) segment a body mark, independently of the target position information, into a plurality of pre-set segmented areas; and (ii) determine a first highlighted area that is one of the plurality of pre-set segmented areas in the body mark based on the target position information,
  wherein the target position information indicates an area including a current lesion or a prior occurrence of a prior lesion in the subject, the indicated area being one of the plurality of pre-set segmented areas in the body mark;
  a display combiner configured to display the body mark including the first highlighted area together with the generated ultrasound image data on a display unit;
  an input unit configured to receive a predetermined input from an operator; and
  an output controller,
  wherein the highlighted-area determiner is configured to determine a second highlighted area that is one of the plurality of pre-set segmented areas in the body mark including a position corresponding to the current lesion or a suspected lesion based on the predetermined input by the operator,
  wherein the output controller is configured to output the first highlighted area and the second highlighted area in a different manner for simultaneous visual observation,
  wherein the input receiver is configured to read the target position information from a first storage unit which stores the target position information on the subject, and
  wherein the highlighted-area determiner is configured to determine the first highlighted area that is one of the plurality of pre-set segmented areas in the body mark based on the read target position information.

2. The ultrasound image diagnostic apparatus according to claim 1, wherein:
  the input unit is configured to receive operation information; and
  the highlighted-area determiner comprises a body-mark divider configured to segment the body mark into the plurality of pre-set segmented areas in accordance with the operation information,
  wherein the highlighted-area determiner is configured to determine the first highlighted area.

3. The ultrasound image diagnostic apparatus according to claim 1, wherein:
  the input receiver is configured to receive the target position information from another diagnostic apparatus, and
  the highlighted-area determiner is configured to determine the first highlighted area that is one of the plurality of pre-set segmented areas in the body mark based on the received target position information.

4. The ultrasound image diagnostic apparatus according to claim 1, further comprising:
  a second controller configured to connect the generated ultrasound image data to the plurality of pre-set segmented areas in the body mark and store resulting data in a second storage unit, the generated ultrasound image data being generated by examinations of sequential scanning of the plurality of pre-set segmented areas in the body mark.

5. The ultrasound image diagnostic apparatus according to claim 1, wherein:
  the highlighted-area determiner is configured to determine an area in a current examination procedure to be a third highlighted area, in examinations performing sequential scanning of the plurality of pre-set segmented areas in the body mark for generation of the generated ultrasound image data to be displayed, and
  the display combiner is configured to display the body mark including the third highlighted area together with the generated ultrasound image data on the display unit.

6. The ultrasound image diagnostic apparatus according to claim 1, further comprising:
  a timing controller configured to count examination time of each of the plurality of pre-set segmented areas,
  wherein the highlighted-area determiner is configured to determine an area corresponding to the examination time counted as longest by the timing controller to be a fourth highlighted area including a position corresponding to a lesion or a suspected lesion, and
  wherein the output controller is configured to output the first highlighted area and the fourth highlighted area for simultaneous visual observation.

7. The ultrasound image diagnostic apparatus according to claim 1, wherein the output controller is configured to display the body mark including the second highlighted area combined with the generated ultrasound image data generated corresponding to the second highlighted area on the display unit.

* * * * *